US009018983B2

(12) United States Patent
Vankov

(10) Patent No.: US 9,018,983 B2
(45) Date of Patent: Apr. 28, 2015

(54) CIRCUIT TO GENERATE HIGH FREQUENCY SIGNALS

(71) Applicant: Medtronic, Inc., Minneapolis, MN (US)

(72) Inventor: Alexander B. Vankov, Menlo Park, CA (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 0 days.

(21) Appl. No.: 13/963,335

(22) Filed: Aug. 9, 2013

(65) Prior Publication Data

US 2014/0002142 A1 Jan. 2, 2014

Related U.S. Application Data

(62) Division of application No. 12/136,683, filed on Jun. 10, 2008, now abandoned.

(51) Int. Cl.
*H03K 3/00* (2006.01)
*H03K 3/02* (2006.01)
*A61B 18/18* (2006.01)
*H03K 17/082* (2006.01)
*H03K 17/691* (2006.01)

(52) U.S. Cl.
CPC *H03K 3/02* (2013.01); *A61B 18/18* (2013.01); *H03K 17/0822* (2013.01); *H03K 17/691* (2013.01)

(58) Field of Classification Search
USPC .......................... 327/108–112, 402–404, 443
See application file for complete search history.

(56) References Cited

U.S. PATENT DOCUMENTS

| 4,493,017 | A | * | 1/1985 | Kammiller et al. | 363/132 |
| 4,937,470 | A | * | 6/1990 | Zeiler | 327/109 |
| 5,371,423 | A | * | 12/1994 | Berthold et al. | 326/57 |
| 5,959,493 | A | * | 9/1999 | Cassista | 327/391 |
| 6,897,707 | B2 | * | 5/2005 | Beck | 327/427 |
| 7,965,522 | B1 | * | 6/2011 | Hornberger et al. | 363/21.1 |
| 2013/0063184 | A1 | * | 3/2013 | Liang et al. | 327/108 |
| 2013/0200926 | A1 | * | 8/2013 | Kihara et al. | 327/108 |
| 2013/0265029 | A1 | * | 10/2013 | Akiyama | 323/311 |

* cited by examiner

*Primary Examiner* — An Luu
(74) *Attorney, Agent, or Firm* — Jeffrey J. Hohenshell

(57) ABSTRACT

Method and apparatus for electrosurgery including tissue coagulation using very high voltage pulses of electrical energy applied to the electrosurgical probe. This minimizes heating of the surrounding tissue in the probe and is especially suitable for precise and limited coagulation and fulguration without excessive tissue charring or other damage. The power at rated load of the applied pulses to the probe is typically over 300W and the duration of the on time is very short, so each group of pulse bursts is of relatively low duty cycle. An RF generator is also provided for delivering electrical energy to an electrosurgical probe with the proper characteristics, including fast switching times.

4 Claims, 7 Drawing Sheets

CIRCUIT TO GENERATE HIGH FREQUENCY SIGNALS

RELATED APPLICATION

This application is a division of and claims priority to U.S. patent application Ser. No. 12/136,683, entitled "METHOD FOR LOW TEMPERATURE ELECTROSURGERY AND RF GENERATOR", filed Jun. 10, 2008.

FIELD OF THE INVENTION

This invention relates to electrosurgery for biological tissue and circuits to generate high frequency signals related thereto.

BACKGROUND OF THE INVENTION

The field of electrosurgery is well known; see for instance, Palanker U.S. Pat. No. 7,238,185 and Palanker, et al. U.S. Pat. No. 6,780,178 both incorporated herein in their entireties. Briefly, application of a voltage to an electrode is useful for cutting, ablating and fulgurating biological tissue. This is generally known as electrosurgery. Typically the voltage is applied as a train of high frequency pulses in the radio frequency (RF) range to a probe in contact with the tissue.

A problem with electrosurgery is preventing excessive application of heat to the tissue being cut, fulgurated, desiccated, etc. since this tends to produce undesirable affects such as charring and collateral tissue damage. This is typically caused by high temperatures induced by, the application of the electrical energy.

Some highly localized high temperature is required during, for instance, tissue coagulation (sealing) for denaturation of blood and vascular tissue (veins and arteries) followed by occlusions of the blood vessels. Typically desiccation occurs below or close to 100° C. and fulguration at higher temperatures above 100° C. A high temperature during fulguration outside the immediate area being treated results in undesirable tissue charring and buildup of debris on the electrosurgical probe, which decreases its efficiency of coagulation. This may also result in adhesion of charred tissue to the probe and damage to the areas of the probe with low melting temperatures such as plastic components. Typically this might require cleaning of the probe after each session of coagulation. Also, high temperature may result in smoke obscuring the surgical field, especially for laparoscopic procedures.

SUMMARY

A method and apparatus for pulsed applications of heat in electrosurgery provide sufficient peak temperature for tissue coagulation (and "blend" cutting) and allow for cooling of tissue between the application of electrical energy pulses, so avoiding excessive heating. Typically groups of pulse bursts are separated by a time interval sufficient for cooling both the probe and immediately neighboring tissue to close to ambient temperature.

In one embodiment this is achieved by using RF high power groups of pulse bursts, such as power levels of 300 W or higher during on time and zero during off time, the groups of bursts being of high frequency such as 100 kHz to 5000 kHz and each group of bursts having a duty cycle in the range of 1% to 50%. Duty cycle refers to the ratio of time when RF power is applied to the rated load to the full duration of the group of bursts. According to this definition a sine wave has a 100% duty cycle. For coagulation and blend cutting electrosurgery, the sine wave cycles (on time) occupy a short time in each burst, with a substantial part of each burst having no RF energy present (off time). A number of such bursts are grouped together, with an interval of at least 1 millisecond between each group of bursts, to allow for tissue cooling. Each burst of pulses has enough electrical power to rapidly heat the tissue to temperatures adequate for coagulation.

The active portion of the electrosurgery probe itself is typically of relatively small size to provide a short cooling time. Moreover the probe is bare metal or metal covered with a layer of insulation, with the layer of insulation defining an opening at the edge where the electrical pulses are actually applied to the tissue for coagulation and cutting and further defining a number of spaced apart small openings on its side surfaces (flat portions), each having a diameter for instance of 0.02 mm to 0.10 mm for extensive coagulation.

An RF pulse generator is used for low temperature electrosurgery tissue cutting. This pulse generator provides square wave alternating positive and negative pulses with a fast switching time and a pulse amplitude of up to 1000 Volts peak to peak. The particular circuit disclosed here, also referred to as a pulse generator or radio frequency generator in the field, is based on a conventional half bridge inverter with high power transistors serving as high and low side switches. In order to overcome the well known problem of Miller capacitance, each channel of the inverter (there being a positive pulse voltage channel and a negative pulse voltage channel) is provided with a gate driver circuit driving the gate of each switching transistor. Moreover an input terminal of the gate driving circuit is negative biased and also coupled to ground via a resistance. Further, each channel also includes a current driver (booster) with a disable function to provide protection of the circuit in short circuit conditions.

BRIEF DESCRIPTION OF THE DRAWINGS

FIG. 6 shows a schematic diagram of a protection circuit used with the RF generator of FIG. 4a.

DETAILED DESCRIPTION

The entire content of U.S. patent application Ser. No. 12/136,683, filed Jun. 10, 2008, is hereby incorporated by reference.

High Voltage Electrosurgery

High voltage RF electrical energy is applied to an electrosurgical probe for tissue coagulation and cutting. It is understood that the electrosurgery probe itself may be of the types disclosed here or in the above described patent applications or other types as known in the field. Typically the probe has a relatively small surface area at its active electrode portion (tip) to minimize heating of the tissue being treated. The probe may be uninsulated (bare metal) or partly covered with a high dielectric insulating layer. The probe may be mono or bi-polar. In some applications the probe is immersed in the tissue being operated on, which has naturally occurring fluid present or some type of liquid is provided immediately around the probe in the surgical field. In other uses for, e.g., fulguration no liquid is present.

Energy is intended primarily for use with electrosurgical coagulation, but can be used for simultaneous tissue cutting and coagulation. For tissue coagulation purposes some amount of charring is in fact desirable since that is the intent of coagulation (to seal tissue). However, tissue charring is undesirable beyond the immediate area being coagulated. The goal is to maintain a relatively low probe temperature and hence minimize heat transfer to the surrounding tissue while still accomplishing coagulation or desiccation or fulguration. Hence the present method is directed to what is sometimes called "cold coagulation."

The edge of the probe is intended for both cutting and coagulation, and the flat (side) portion thereof with "dimples" (the openings) serves for coagulation only. As the probe edge cuts through the tissue, the flat portion of the probe sends an electrical arc to the walls of the wound to heat and close the blood vessels. The dimples help the electrical arc to reach all blood vessels, as in an uninsulated probe, but the small diameter of the dimples advantageously provides a short thermal relaxation time and, as a result, low temperature during pulsed coagulation.

This is accomplished here by applying high power RF groups of bursts with relatively long off times and thus relatively low duty cycles compared to conventional electrosurgical coagulation. While equipment limitations may prevent use of RF power levels above 300 W given current materials and electrical components, ultimately this is not limiting. Hence generally, the present invention is directed to use of high rated power RF (above 300 W) during the pulse on time. Since power depends on the load, the rated load is by definition the load where the maximum (rated) power can be achieved. A typical voltage here (both positive and negative) is up to 12,000 Volts peak to peak under open circuit conditions. A typical waveform for this condition is a damped sine wave.

Figure 1A:
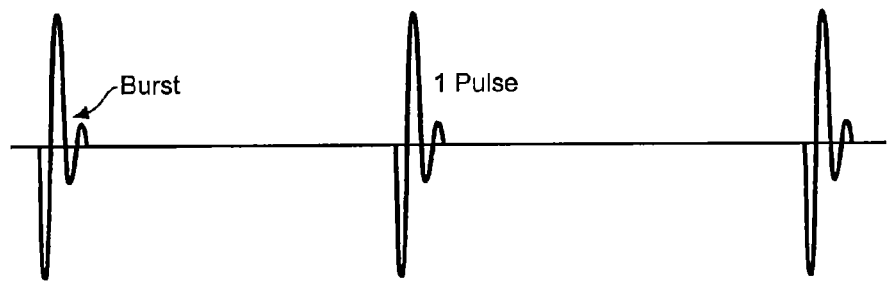
FIGS. 1a, 1b, 1c show a set of high power groups of bursts indicating the nature of the electrical energy applied to the probe in accordance with the invention for 3 types of coagulation respectively spray, pinpoint, and blend.
Figure 1B:
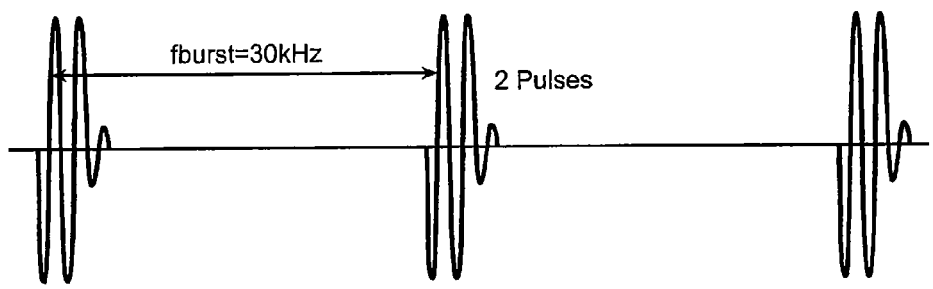
Figure 1C:
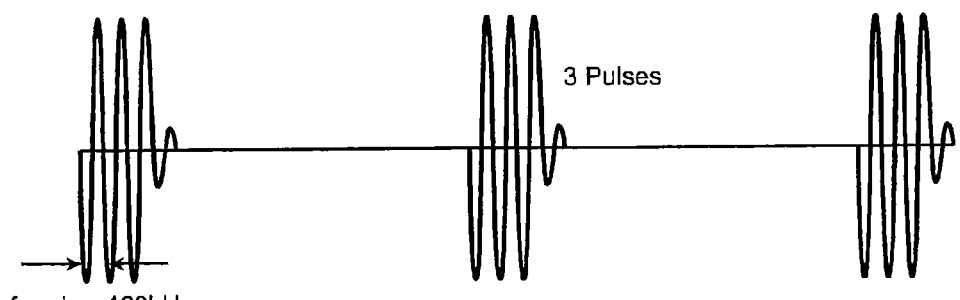

In one embodiment the RF power has a carrier frequency of approximately 460 KHz, so the duration of each period (pulse) is approximately 2.2 microseconds. The on time RF pulses can be sine waves, but usually a sine wave is good only for pure cutting. For blended cut and coagulation purposes, periods of pulses are clustered in each burst with no RF energy between them. In one embodiment, there is only one period per burst but this is not limiting; there may be 2, 3, or more pulses per burst as shown respectively in FIGS. 1a, 1b, 1c for different types of coagulation. The repetition rate for the bursts is e.g. 30 KHz. A typical frequency for the groups of burst is 25 Hz. A group of these bursts defines the on time, followed by the off time. Hence the duty cycle of each group (during on time) is in the range of 1% to 50%. That is, only 1% to 50% of the total time during each group of bursts is actually occupied by RF energy and the remainder is of zero voltage applied to the load, as shown in FIGS. 1a, 1b, 1c. A number of such pulse bursts may also be grouped together. Typically the off time between each group of bursts is about 1 millisecond or more to allow further cooling of the probe and associated tissue. The on time can be from 100 microseconds to 10 ms, followed by the off time off interval, at least 1 ms in duration. This modulation further reduces the duty cycle by a factor of 0.01 to 0.9.

The open circuit waveform is, e.g., a damped sine wave at the carrier frequency (such as 460 kHz in FIG. 1c) which shrinks to a sine wave cycle as shown in FIG. 1a at a low impedance load. The amplitude (voltage) of these pulses decreases with the resistance of the load in such a way that the average RF power achieves a maximum at a so called "rated load", typically 100 to 1000 Ohm. The time T between pulse centers corresponds to the inverse of the carrier frequency (for example T=1/460 kHz). The number of pulses in a pulse burst determines the rated load, roll-off points on the load curve, the type of the surgical mode (called in the field, for instance, blend, desiccation, fulguration), and the length of the spark. The repetition rate of the pulse bursts is typically 20 to 60 kHz (indicated as burst of 30 kHz in FIG. 1b). The purpose of these bursts is not a cooling of the tissue during the burst off time, since tissue temperature cannot decrease during mere tens of microseconds. Instead the off time allows for collapse of undesirable vapor bubbles formed on or near the probe, arising during the pulse on time. Otherwise due to the vapor bubbles the tissue experiences problematic "micro explosions" of the bubbles, repulsing tissue from the probe, and precluding effective coagulation.

Figure 2:
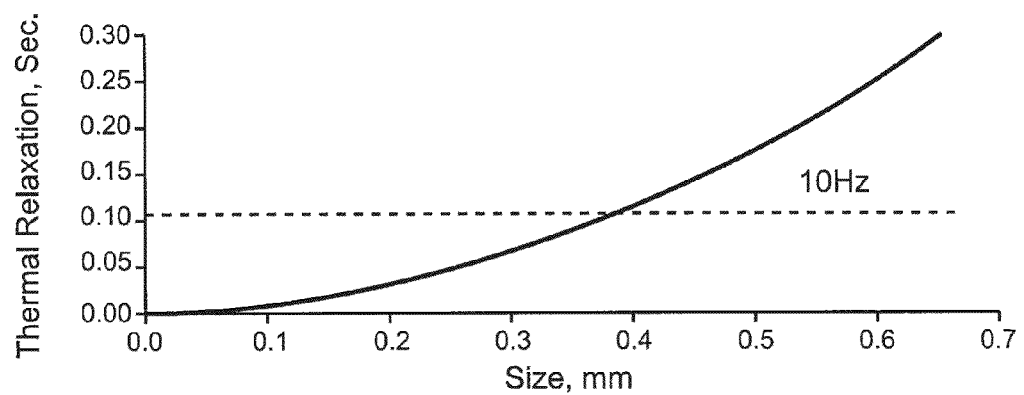
FIG. 2 shows a graph of thermal relaxation time vs. probe size.

In the present method therefore for coagulation the pulse bursts are grouped together, with a time interval between them (determined by the burst duty cycle) longer than the thermal relaxation time for a particular probe. The thermal relaxation time t can be assessed as $t=r^2 c\rho/\pi^2 k = r^2 0.7 \, \mu s/\mu m^2$, where r is the characteristic size of the electrode in µm, c is heat capacity, ρ is density, and k is thermal conductivity of liquid as plotted in FIG. 2. For instance, for a 10 µm effective probe electrode size the thermal relaxation time is 701 µs, but for 1 mm probe this value is 0.7 seconds. So, a small probe electrode is generally required here.

The small probe can coagulate only a small area adjacent to the probe electrode. With a spark (arc) length of 1 mm and a point electrode that is 0.1 mm in diameter, one can coagulate a spot of tissue 2.1 mm in diameter. Multiple small electrodes, representing small openings in the probe insulation are introduced on the flat portion of the blade and spaced apart to coagulate a large solid area of tissue. The spark circles should overlap to cover the whole tissue surface. The size of the individual electrodes (the openings) is small enough to provide fast cooling. At pulsed mode as described above, low average tissue temperature can be achieved. As a result, the probe provides shallow strong coagulation with a safe temperature of the probe.

Figure 3:
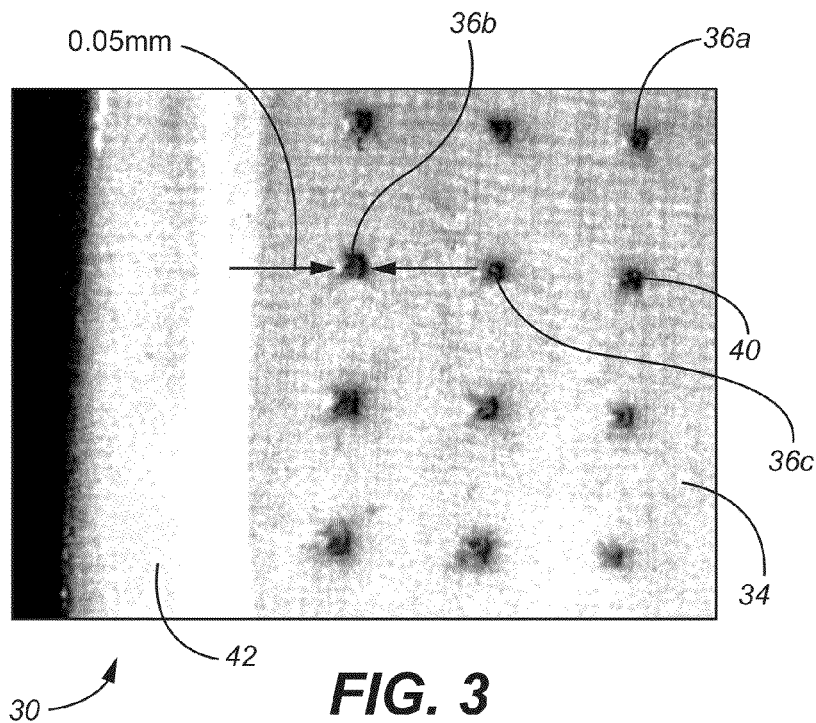
FIG. 3 is a planar view of a portion of an electrosurgical probe showing the openings defined on the side surfaces of the probe through the insulation layer.

FIG. 3 shows a partial view of a side surface of the associated probe 30 in which the overlying insulating layer 34 defines a pattern of openings (dimples) 36a, 36b, 36c, etc. to expose the underlying metal 40 of the electrode of probe 30. In this case the size of each opening is shown as about 0.05 mm by 0.05 mm (each being approximately a square), however, this size and shape are not limiting. The spacing between openings (center to center) is in the range of 0.2 to 1.0 mm, not limiting. Also conventionally the metal edge 42 of probe 30 is also exposed through the overlying insulating layer 34. The actual materials of the probe metal 40 and insulation 34 are conventional as explained in the above referenced patents and as well known in the field.

Typically the associated equipment (RF generator) has variable outputs and can be adjusted by the operator to provide pulses of various frequencies and timing durations so that the present pulse regime is thereby accomplished. This pulse regime may depend on probe size, the nature of the surgical procedure being undertaken such as fulguration, desiccation, coagulation, and other factors as determined by the operator (surgeon). A typical range of correct frequencies for the pulses is 100 KHz to 5 MHz, of which the above described 460 KHz is merely illustrative. In accordance with this approach, the probe and the associated tissue may be kept below or above 100° C., depending on what is required for the particular surgical procedure being undertaken. Advantageously the relatively low temperature of the probe-tissue interface results in reduced adhesion of the charred tissue to the probe, decreasing smoke and providing better performance for coagulation.

RF Generator

An RF generator 50 for e.g. pulsed cutting of tissue (see circuit diagram FIG. 4a), is compatible with a pulsed coagulation method and probe described above. Such an RF generator is believed to be novel for electrosurgery, where out coupling typically represents a transformer, although generally RF generators are well known in the electronics field for generating high frequency electrical signals. Such RF generators typically are half bridge inverters. The present RF generator has only capacitors in series with the load as required by regulatory rules (for a capacitance <5 nF), and the usual RF transformer is omitted. Associated waveforms are described in Palanker U.S. Pat. No. 7,238,185, incorporated herein by reference in its entirety, and represent a true bipolar square wave. The present RF generator for tissue cutting may be a part of a system producing also coagulation waveforms according to FIGS. 1a, 1b, 1c to combine cutting and coagulation ability for a single probe.

In accordance with similar circuits, the present RF generator apparatus or circuit 50 conventionally includes a half bridge inverter with high power Field Effect Transistors (FET) Q2, Q1 used as respective low and high side switches. In such an RF switching generator or power supply the amount of time for each switch (transistors Q1, Q2) to turn on or off is important. For proper performance the switching transistors should be capable of switching in less than approximately 10% of the period of the output pulse. For a 4 MHz frequency pulse this requires that each transistor's Q1, Q2 gate terminal be charged/discharged in less than 25 nanoseconds.

As well known in the field, the effective gate capacitance or input capacitance of such field effect transistors Q1, Q2 includes the gate-source capacitance and the gate-drain capacitance, also referred to as Miller capacitance. The total gate charge required to charge the gate of a typical field effect transistor from 0V to 3V (enough to switch the transistor) is 80 nC. This total charge includes the Miller charge required to discharge the gate-drain capacitance when the transistor switches from the off state with a drain-source voltage of 450V, to the on state. If the entire charge is to be delivered in a 25 nanosecond period as indicated above, then the gate driver circuit which provides the signal to the gate must apply an average current of 80 nC/25 ns=3.2 amps with a peak current as high as 12 amps. To meet this, the gate driver circuits 52, 54 in this generator are selected to provide a 20 amp maximum current, but this is merely illustrative.

For typical electrosurgery applications, the electrical charge injected in the tissue from the probe must be close to zero to minimize undesirable muscle stimulation. Thus it is important to have balanced positive and negative portions of the pulsed current provided to the probe. In the present RF generator therefore two channels 58, 60 are used, e.g., connected to two Direct Current (DC) power supplies (not shown), one providing +500V and the second providing −500V output signals at respectively nodes 115, 117. The output terminal 112 (to the probe) for generator 50 therefore is connected at a midpoint node 66 between the two channels 58, 60. Voltage at this terminal 66 therefore swings between positive and negative voltages as described further below.

The current driving for the gate of each switching transistor Q1, Q2 is provided here with a radio frequency isolated independent driving direct current power supply. The RF isolation is required because the gate of each transistor Q1, Q2 is referenced to the source of the transistor, which switches with slew rates of more than 30 Volt/nanosecond. The high side driving reference point 66 has to have a minimum coupling capacitance and leakage inductance to the ground of the drivers 52, 54.

Transformers 78, 80 are provided as is conventional in each channel 58, 60 for galvanic isolation and level shifting required for each switching transistor Q1, Q2. An advantage of this is at the high-side gate driver circuit 52 does not require a floating power supply since the power to transistor Q1 is coupled through the transformer 78. The leakage inductance of the windings of each transformer 78, 80 makes it difficult to obtain the rapid rise of the current required and causes excessive ringing which must be suppressed. Improved operation is obtained here by using a large sinusoidal drive current since the leakage inductance of the transformers 78, 80 along with the input capacitance of each transistor Q1, Q2 can be included in a resonant circuit.

Figure 5A:
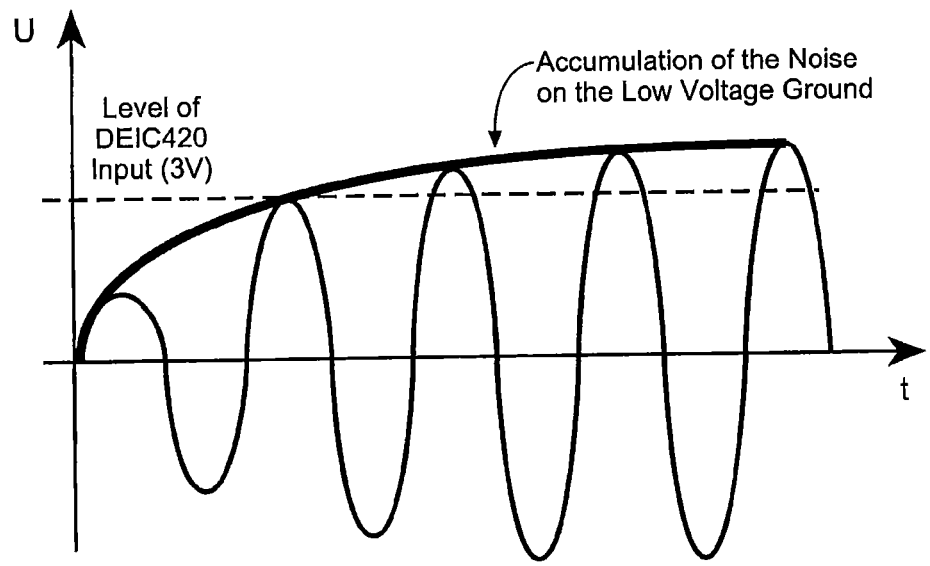
FIG. 5a shows the potential problem of noise in the present RF generator.

In this case the sine wave output of the resonant circuit has higher amplitude than the transistor switching threshold voltage, to minimize switching time. However, fast switching results in shorter high voltage swings on the source/drain terminals of the switching transistors Q1, Q2. Short intense transients therefore travel back from the mid-point 66 of the half bridge to the gate terminals of transistors Q1, Q2 due to the Miller capacitance into the output of each gate driver circuit 52, 54 from each of the transformers 78, 80. Each gate driver circuit 52, 54 has a 0.6 Ohm output resistance in both high and low output voltage regimes. Therefore the energy of the transient goes mostly to the low voltage ground as indicated in FIG. 5a and causes ringing. This undesirable ringing may affect the input of the gate driver circuits 52, 54 causing simultaneously opening and closure of the switching transistors Q1, Q2 which, of course, must be avoided. In order to increase signal to noise discrimination level and avoid ringing, a negative bias voltage as shown of −1V is applied to the input ("In") terminal of each gate driver circuit 52, 54. Additionally in this case the same input terminal of each gate driver circuit 52, 54 is also coupled to ground via a low resistance (22 Ohm) resistor 80, 82. Also, 22 Ohm resistors 86, 88 are coupled across the primary and/or secondary windings of each transformer 78, 80 to damp ringing. Also, to decrease quality factor of the resonant circuit, inductances of the primary and secondary windings of each transformer 78, 80 are chosen to be minimal e.g. 1.6 microH. With the input capacitance of the MOSFET Q1, Q2 (1 nF) resonant frequency of the contour $f=1/(2\pi(LC)^{0.5})=4$ MHz is equal to the operation frequency. The inductance of the ground path to the input terminal of each gate driver circuit 52, 54 is minimized with short and wide leads. Also, a DC/DC converter 90, 92 is coupled to the input terminal of each gate driver circuit 52, 54 to create the above mentioned negative direct current bias of −1 Volt to that input terminal and effectively discriminate noise at the input terminal of each gate driver circuit 52, 54.

Figures 1, 4A:
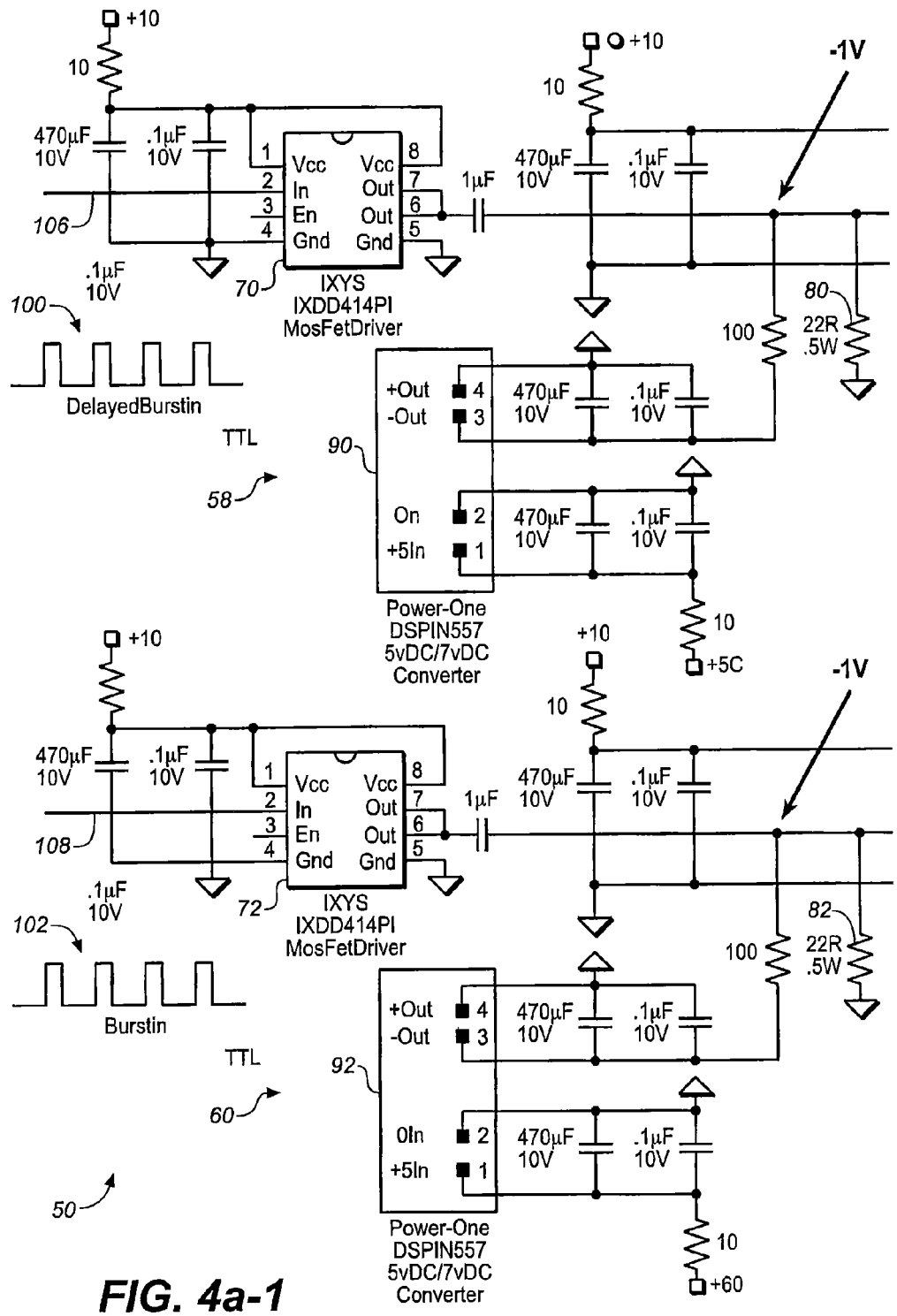
FIG. 4a is a schematic circuit diagram of a RF generator in accordance with the invention.
Figures 2, 4A:
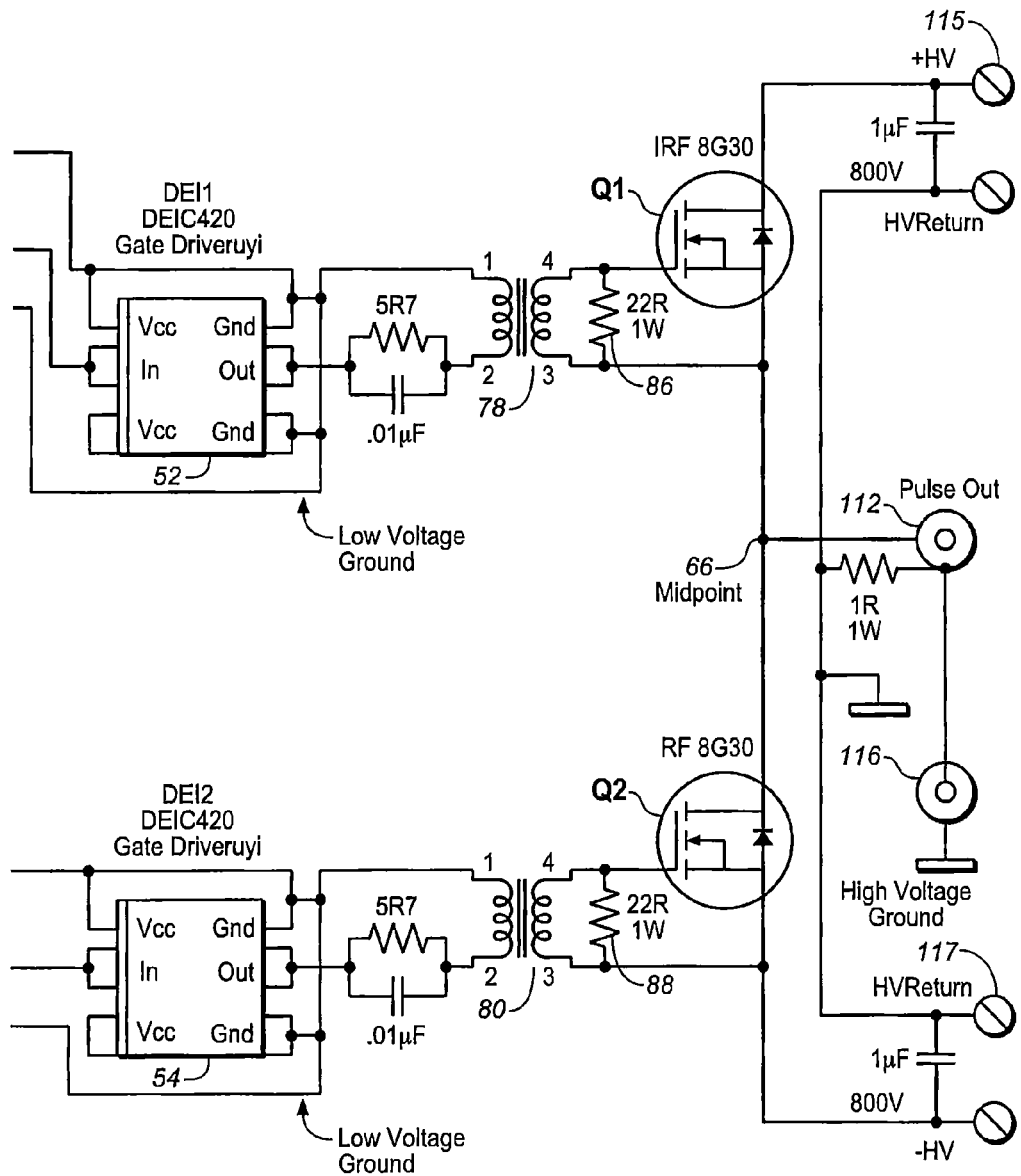
Figure 4B:
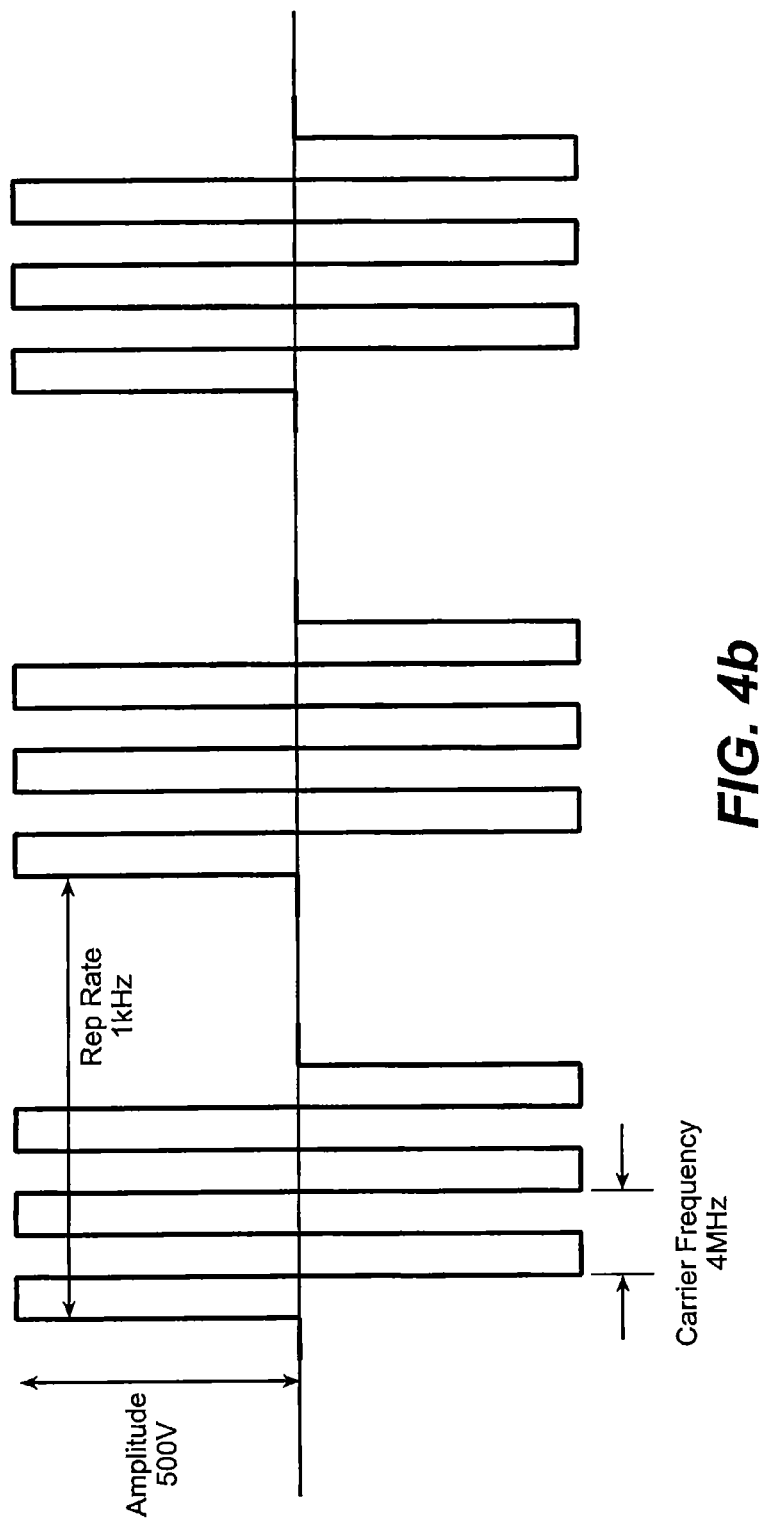
FIG. 4b shows an output waveform of the RF generator.

As shown in FIG. 4a, effectively the negative input bias at the input terminal "In" of each gate driver circuit 52, 54 is −1 Volt in this example. In the left hand portion of FIG. 4a are shown (as waveforms) the input control signals 100, 102 applied to each input terminal 106, 108 of the two channels of the RF generator and shown as a set of square waves which determines timing for the pulse bursts and pulses as explained above. The input control signals are generated conventionally. Conventionally in the far right hand portion of FIG. 4a is the RF generator output terminal 112 labeled "pulse out" which is connected to the probe. FIG. 4b shows an output waveform (at node 112) of the RF generator 50. Also provided is a high voltage ground terminal 116 connected to the probe ground terminal or to a return line connected to the patient. The remaining circuit elements in FIG. 4a are conventional; in some cases component numbers or values are shown, but these are only exemplary.

Figure 5B:
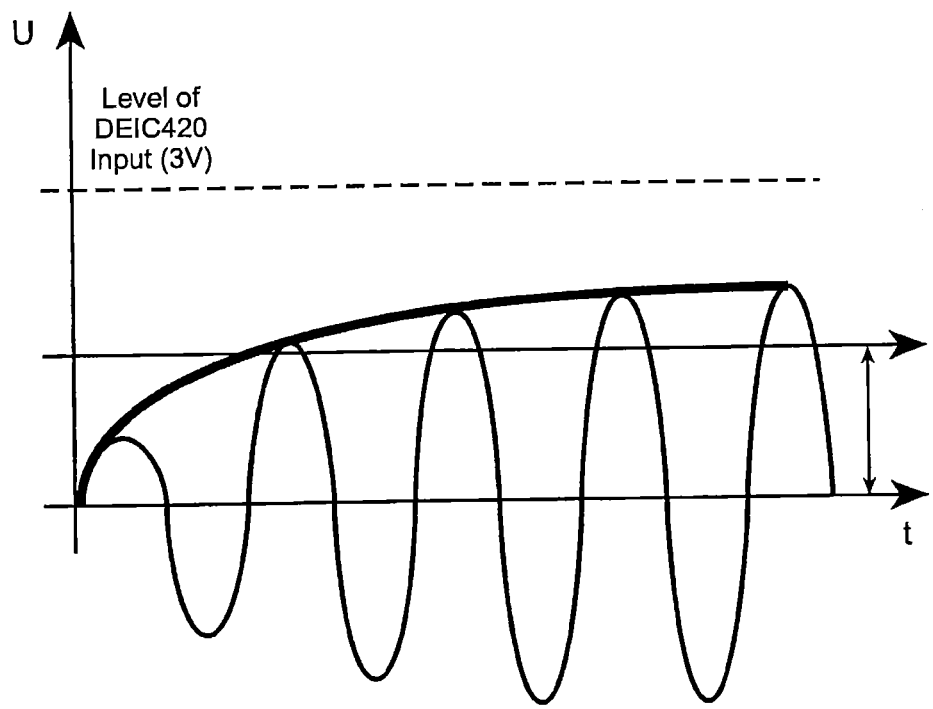
FIG. 5b shows how the problem of noise is overcome in accordance with the present RF generator.

FIG. 5a shows via waveforms how the circuit of FIG. 4a would have an accumulation of noise on a low voltage ground resulting in an uncontrollable wave form, e.g., due to ringing. The horizontal axis here refers to time and the vertical axis is the voltage at the input terminal of each gate driver. The horizontal broken line at 3 Volt is the threshold voltage at the input terminal of the gate drivers 52, 54. FIG. 4b shows how the above described negative bias of −1 Volt applied to that same input terminal (and also shown as the horizontal broken line in FIG. 5b) reduces the amount of noise compared to FIG. 4a at the In terminal to the gate driver circuits 52, 54.

Figure 6:
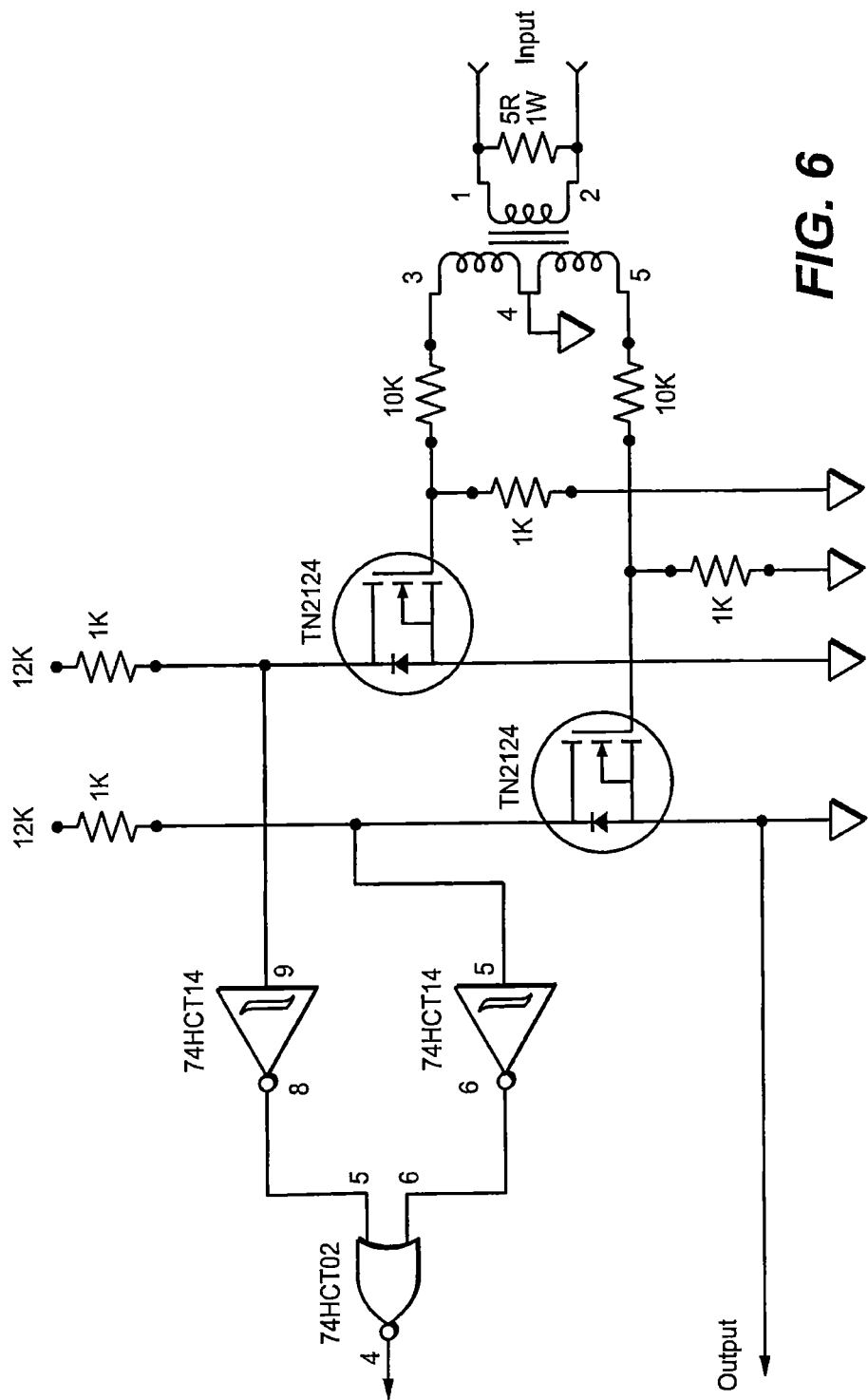

In one embodiment, the circuit of FIG. 4a provides over current protection to prevent damage to the switching transistors and/or the other components. Typically failure of such a RF generator is caused by excessive currents flowing either through the switching transistors or into the output terminal. Various conventional protection circuits are known and an example is shown in FIG. 6 which would be coupled conventionally to generator 50. These protection circuits typically include current transformer sensors connected either to the return patient cable (ground to the patient, e.g., at node 116) or to the high voltage lines at node 112. The circuit of FIG. 4a since it has two channels 58, 60 would typically have two such protection circuits, one coupled to each channel 58, 60.

This description is illustrative and not limiting. Further modifications and improvements will be apparent to those skilled in the art in light of this disclosure and are intended to fall within the scope of the pending claims.

What is claimed is:

1. A circuit to generate high frequency signals, comprising:
   a first channel and a second channel, each including a switching transistor, an output terminal of each transistor being coupled to a common output node;
   a control terminal of each transistor being coupled to an output terminal of a driver; and an input terminal of each driver being coupled to a source of a negative voltage bias;
   wherein the first channel provides positive going signals at the common output node and the second channel provides negative going signals at the common output node.

2. The circuit of claim 1, further comprising coupling the input terminal of each driver to ground.

3. The circuit of claim 2, further comprising:
   a current driver circuit having an output terminal coupled to the input terminal of each driver.

4. The circuit of claim 2, further comprising a current protection circuit coupled to each channel.

* * * * *